United States Patent [19]

Ramsay et al.

[11] 4,182,756

[45] Jan. 8, 1980

[54] HIGH CALORIE SOLUTIONS OF LOW MOLECULAR WEIGHT GLUCOSE POLYMER MIXTURES USEFUL FOR INTRAVENOUS ADMINISTRATION

[75] Inventors: Anne B. Ramsay, Ingleside, Ill.; Delbert R. Luebke, Kenosha, Wis.; David T. Guzek, Wildwood, Ill.; Chia-Lung Hsieh; Robert Roteman, both of Waukegan, Ill.; William D. Leathem, Lindenhurst, Ill.

[73] Assignee: Abbott Laboratories, North Chicago, Ill.

[21] Appl. No.: 853,366

[22] Filed: Nov. 21, 1977

[51] Int. Cl.² ............... A61K 31/715; C07H 1/00; C08B 37/00
[52] U.S. Cl. ............... 424/180; 424/177; 536/1; 536/4
[58] Field of Search ............... 424/180; 536/1, 4

[56] References Cited

U.S. PATENT DOCUMENTS

| 3,928,135 | 12/1975 | Milner | 424/180 |
| 4,021,543 | 5/1977 | McKay | 424/180 |

OTHER PUBLICATIONS

Berlyne, et al., "The Lancet", Apr., 1969, pp. 689–692.
Bott et al., "The Pharmaceutical Journal", May, 1970, pp. 583–584.

*Primary Examiner*—Johnnie R. Brown
*Attorney, Agent, or Firm*—Robert L. Niblack; Aaron L. Hardt

[57] ABSTRACT

High calorie solutions of low molecular weight glucose polymer mixtures useful for intravenous administration, preferably via a peripheral vein, are disclosed. Methods of preparing the solutions and their preferred rate of infusion at less than 5 mg./min./kg. of patient body weight are also disclosed. The solutions can be isotonic to human blood at 20–50% W/V as the glucose polymer mixtures have an average degree of polymerization ranging from 4 to 10. At the preferred rate of infusion high utilization of the glucose polymers infused occurs in human patients, including diabetics. The utilization can be further enhanced by concomitant injections of insulin. The solutions can be administered concomitantly with amino acids, lipid emulsions, vitamins and electrolytes.

46 Claims, No Drawings

HIGH CALORIE SOLUTIONS OF LOW MOLECULAR WEIGHT GLUCOSE POLYMER MIXTURES USEFUL FOR INTRAVENOUS ADMINISTRATION

BACKGROUND OF THE INVENTION

The present invention relates to high calorie solutions for intravenous administration to human patients and methods of administering such solutions. More particularly, the present invention relates to solutions comprising glucose polymer mixtures of low molecular weight which can be infused into and utilized by human patients in relatively high concentrations without requiring use of a central vein. The present invention further relates to methods of preparing the high calorie solutions and preferred rates of their infusion. Still further, the invention relates to the utilization of the solutions by diabetic human patients.

Major nutritional problems are seen in many human patients who for one reason or another cannot obtain an adequate supply of calories by mouth. The problems are particularly acute in unconscious patients, surgical patients who have lost a large amount of weight preoperatively, and in patients in protracted convalescence for such diseases as bowel obstruction, peritonitis, or intestinal fistulae.

Because the patient requires energy to maintain life and must constantly synthesize protein tissue, it is essential that the patient's caloric and protein intake be maintained at least at minimum levels. In the absence of any exogenous source of nutrition, the patient will obtain needed calories by catabolism of endogenous fat stores and protein tissues. This can lead to death by starvation, lack of resistance to infection, respiratory muscle failure, or cardiac muscle failure. Accordingly, the intravenous administration of nutrients to the patient can be life-saving.

Conventionally, aqueous solutions of glucose or fructose have been infused into patients intravenously to provide exogenous calories. Because of the osmotic relationship between human plasma and blood corpuscles, an important consideration of any solution parenterally administered to a patient is that it can cause damage to the patient's corpuscles if it is not substantially isotonic to human blood. If the patient's plasma becomes strongly hypertonic, the corpuscles shrivel. If it becomes strongly hypotonic, the corpuscles swell and may burst. Accordingly, the aqueous solutions of glucose or fructose most commonly intravenously infused into a patient are such isotonic 5% W/V solutions.

One liter of 5% W/V glucose solution provides 50 grams of glucose per each 1000 ml. of solution. Each gram of glucose provides 3.4 calories and, therefore, one liter of a 5% W/V glucose solution provides 170 calories per each 1000 ml. of solution. Generally, adult patients require a total of 2,000–5,000 calories per day. To satisfy that need, a patient would have to receive from 12-35 liters of 5% W/V glucose solution per day. Clearly, such an infusion of 12-35,000 ml. of water would grossly over-hydrate the patient.

Alternatively, hypertonic glucose or fructose 10 to 20% W/V solutions can and have been intravenously injected in order to provide the patient more calories. However, their infusion for extended periods of time is limited by the inability of the patient's peripheral veins to handle such hypertonic solutions without serious venous thrombosis or thrombophlebitis resulting.

It is well known that 25-50% W/V solutions of glucose or invert sugar have been intravenously administered to patients via a cannula inserted into the vena cava. While this technique provides a means by which the patient may intravenously receive high calorie solutions, it is not totally satisfactory in that insertion of the cannula is a surgical procedure not generally performed by a nurse, or many surgeons, and the dangerous possibility of septicemia or serious thrombosis in the vena cava, as well as potential damage of the heart and large vessels by the catheter tip.

U.S. Pat. No. 3,067,098 granted Dec. 4, 1962 to W. Pool and entitled "Intravenous Nourishment of Patients" discloses a high calorie solution that could be administered into a peripheral vein by virtue of a small amount of an anti-inflammatory steroid hormone such as hydrocortisone, cortisone, prednisolone, or prednisone included in the solution. The technique disclosed by Pool has not been widely practiced, however, because of the undesirable amounts of steriods that would be administered with prolonged usage.

U.S. Pat. No. 3,793,461 granted Feb. 19, 1974 to S. Yuen and entitled "Intravenous Administration of Maltose to Diabetics" discloses that glucose polymers of D.P.=2 (maltose) can be intravenously administered via a peripheral vein of a patient and that the maltose administered is utilized by human patients by a mechanism unknown to Yuen. The Yuen patent supports the findings of the present invention that glucose polymers can be utilized when intravenously administered into human patients. However, the use of maltose for intravenous therapy is somewhat limited by the fact that isotonic solutions of maltose supply only twice the calories of isotonic solutions of glucose and the relatively high cost of sufficiently pure maltose for intravenous administration.

U.S. Pat. No. 3,928,135 granted Dec. 23, 1975 to J. Milner and entitled "Process for the Production of Glucose Polymers" discloses that glucose polymer mixtures consisting of 3% glucose and glucose polymers of D.P. 2-10 can be administered intravenously. Milner further discloses an oral glucose polymer mixture which has a significant proportion of its molecules of a D.P. greater than 10.

An article by D. Bott, et al. at pp. 583–84 of *The Pharmaceutical Journal* of May 30, 1970 reported the consideration of a glucose polymer mixture, CALOREEN, for possible intravenous use. CALOREEN, which is an orally administered glucose polymer mixture, is reported to consist of 3% glucose, 7% maltose, 5% maltotriose and 85% polysaccharides having molecules of four to fifteen glucose units (A.D.P.=5) at p. 620 of an article by G. Berlynne, et al. entitled "A Soluble Glucose Polymer for Use in Renal Failure and Calorie Deprivation States".

Accordingly, it is clear that a nontoxic metabolizable high calorie solution that can be infused into a patient via a peripheral vein without causing venous thrombosis, thrombophlebitis, or other undesired side effects is needed.

SUMMARY OF THE INVENTION

Therefore, it is the primary object of this invention to provide a high calorie solution suitable for administration into a peripheral vein of a human patient. Preferably, the solution will provide substantially more calories than conventional intravenous solutions per ml. of water administered.

As already discussed, the most limiting factor in intravenous therapy is the inability of the patient's peripheral veins to handle fluids with high osmotic pressure. Osmosis is the passage of water through a semipermeable membrane due to differences in the number of molecules of dissolved substances on the two sides of the membrane. Osmotic pressure is directly proportional to the number of molecules in solution, without regard to the weight of the molecules.

Thus, if all the molecules of a 5% W/V glucose solution were individually replaced by glucose polymer molecules containing two glucose units (maltose), the osmotic pressure of the solution would remain the same, even though the weight of each molecule would have been doubled. Such a maltose solution would, therefore, constitute 100 grams/1000 ml., which is a 10% W/V solution. Further, each molecule would provide two glucose units, so that if the human body can utilize intravenously administered maltose, such a maltose solution would provide twice as many calories as the 5% W/V glucose solution.

Similarly, replacing the molecules of a 5% W/V glucose solution with maltotriose molecules would create a 15% W/V solution providing three times as many calories, while maltotetraose would create a 20% W/V solution providing four times as many calories. Thus, it will be seen that a solution containing X grams/1000 ml. of glucose will be isotonic with a solution containing X grams times the degree of polymerization (D.P.) of a glucose polymer/1000 ml. and further that the glucose polymer solution can provide increased calories of an amount equal to its D.P. times the number of calories provided by the glucose solution.

Likewise, if 20% of the molecules of a 5% W/V glucose solution were individually replaced by glucose polymer molecules containing two glucose units, another 20% by glucose polymer molecules containing three glucose units, a third 20% by glucose polymer molecules containing four glucose units and a fourth 20% by glucose polymer molecules containing five glucose units, the osmotic pressure of the resulting glucose polymer mixture solution would remain the same. However, the weight of the molecules in the solution will have tripled; i.e., 20% same plus 20% doubled plus 20% tripled plus 20% quadrupled plus 20% quintupled equals 300% increase. The average degree of polymerization (A.D.P.) of such a glucose polymer mixture refers to the average number of glucose units per molecule of the mixture. The average degree of polymerization for the above-described glucose polymer mixture is readily calculable as 3.

For the reasons already explained, it will be clear that a maltotriose (D.P.=3) solution isotonic with the above-described glucose polymer mixture (A.D.P.=3) solution would also have a weight triple that of an isotonic glucose solution. Thus, it will be seen that glucose polymers and glucose polymer mixtures of equal D.P. and A.D.P. are isotonic at the same weights and will provide equal amounts of calories if they are equally utilized by the human body.

Accordingly, there is provided by the present invention novel low molecular weight glucose polymer mixtures which can be used to prepare substantially clear, nonpyrogenic, stable and sterile high calorie solutions suitable for administration to human patients, including diabetics, via a peripheral vein. The solutions can be isotonic to human blood at 20–50% W/V as the glucose polymer mixtures can have an average degree of polymerization ranging from 4 to 10. The high calorie solutions are suitable for admixture with amino acids, lipid emulsions, vitamins and electrolytes.

Maximum utilization of the glucose polymer mixtures has been found to occur at rates of infusion less than 5 mg./min./kg. of patient body weight. Utilization of the glucose polymer mixtures is enhanced by concomitant subcutaneous injections of insulin for both diabetic and nondiabetic patients.

Preferred methods of preparing the glucose polymer are by either solvent extraction or molecular membrane filtration of certain commercially available dried corn starch hydrolysates or their equivalents.

DETAILED DESCRIPTION OF THE INVENTION

Mixtures of glucose polymers can be prepared by the hydrolysis of starch. Starch consists of at least two known fractions, amylose and amylopectin, that consist of chains of glucose units. It is well known in the art of starch hydrolysis that the linkages between the glucose units are susceptible to both acid and enzyme hydrolysis and both are routinely employed in the industrial preparation of starch hydrolysates. Because the properties of a starch hydrolysate are dictated by the method of its hydrolysis, starch hydrolysates are characterized as acid treatment, enzyme treatment, and acid-enzyme treatment hydrolysates. It is well known that such starch hydrolysates are useful orally as foods because of their sugar content, while U.S. Pat. No. 4,021,543 granted May 3, 1977 to G. McKay discloses their use as a taste disguising agent.

U.S. Pat. No. 3,663,369 granted May 16, 1972 to A. Morehouse, et al. and entitled "Hydrolysis of Starch" contains an extensive review of the art of starch hydrolysis and the teachings of that patent, including the novel starch hydrolysate products and processes taught therein, are hereby incorporated into this application by this reference to that patent. The teachings of U.S. Pat. No. 3,560,343 granted Feb. 2, 1971 to F. Armbruster, et al. and entitled "Low D.E. Starch Conversion Products" are also incorporated into this application by this reference thereto. While the starch hydrolysates taught by both U.S. Pat. Nos. 3,663,369 and 3,560,343 are intended for oral use, when further fractionated and refined, they serve as excellent raw materials for the substantially clear, nonpyrogenic, stable and sterile intravenous solutions of this invention.

It will be well understood that starch hydrolysates contain a heterogeneous mixture of glucose and polyglucose molecules having a wide range of numbers of glucose units per molecule. In this application, the term "glucose polymer" will be used to mean only polyglucose molecules, while the term "glucose polymer mixture" will be used to describe a mixture wherein glucose may also be present.

According to the present invention, it has been found that a glucose polymer mixture having at least 99% of its molecules less than 26 glucose units, at least 85% of its molecules less than 11 glucose units and at least 20% of its molecules less than 4 glucose units can be utilized by a human patient when intravenously administered via a peripheral vein of the patient. Surprisingly, it has been found that maximum utilization of the glucose polymers occurs at infusion rates of 5 or less mg./min./kg. of the patient's body weight and that total utilization of the mixture may occur at infusion rates of 2.0 to 3.0 mg./min./kg. of the patient's body weight. Higher rates of infusion apparently exceed the rate at which the material can be metabolized, as polymeric material appears in the urine of the patient at such rates. Further, it has been found that the utilization of glucose polymers and glucose polymer mixtures is enhanced by concomitant injections of insulin, in contradiction of the findings of the Yuen patent.

As explained in the above-referenced patents of Morehouse, et al. and Armbruster, et al., hazing is a serious problem in low dextrose equivalent starch hydrolysates due to retrogradation or reassociation of the molecules of higher D.P. with other molecules of higher D.P. to form large relatively insoluble aggregates. It will be realized that the presence of such aggregates in a solution to be intravenously administered must be minimized. Therefore, the glucose polymer mixtures in the solutions of the present invention are selected for their ability to remain stable and provide a substantially haze-free or clear solution.

A further important consideration of a solution to be intravenously administered is the requirement that it be free of fever causing materials called pyrogens, particularly heat-stable polysaccharides, which cannot be removed by autoclaving. The glucose polymer mixtures of this invention have such pyrogens removed by filtration techniques during the final preparation of the solution.

Still another important consideration of the suitability of a glucose polymer mixture for inclusion in the high calorie intravenous solutions of this invention is the ability of the mixture to remain stable during steam sterilization or autoclaving. If the mixture would substantially retrograde during autoclaving, the aggregates so formed and evidenced by hazing of the solution would render the solution totally unusable for intravenous administration. To the contrary, if the mixture would degrade, the number of molecules of lower D.P. could increase to the point that the average degree of polymerization would be reduced, thereby reducing the number of calories obtainable from an isotonic solution of the mixture.

Likewise, the stability of the glucose polymer mixture selected for the solutions for intravenous administration of the present invention is critical to the admixture therewith of additional nutrients such as 3.5–10% W/V amino acids, 5–20% W/V lipid emulsions, vitamins and electrolytes. Preferably, the solutions of the present invention can be so mixed and stored in a suitable container prior to the administration thereof. It will be obvious to those skilled in the art that such nutrients can also be concomitantly administered to the patient from another container or solution.

Generally, with respect to glucose polymers, the term "low molecular weight" is understood to include molecules of D.P.=1–14, while the term "intermediate molecular weight" is understood to include molecules of D.P.=15–25, and the term "high molecular weight" is understood to include all molecules greater than D.P.=26. The average degree of polymerization of the glucose polymer mixtures selected for the high calorie solutions of the present invention is from 4 to 10. Thus, it will be apparent that the mixtures have an average low molecular weight.

The importance of infusing solutions isotonic with human blood has already been explained hereinabove. Based on that explanation, it will be apparent that a glucose polymer mixture having an A.D.P. of 4 will be isotonic with blood in a 20% W/V solution, while a glucose polymer mixture having an A.D.P. of 10 will be isotonic with blood in a 50% W/V solution. While it is true that the primary object of this invention is to provide high calorie solutions for intravenous infusion via a peripheral vein, it will readily be obvious to those skilled in the art that the novel solutions of this invention can be used in nonisotonic solutions, if desired, e.g., in a vena cava infusion.

When the novel solutions of this invention were injected into human patients, it was found that they are utilized by means other than the glucose/insulin route. Laboratory evidence indicates that phosphorylase A may be important in the metabolism of glucose polymers, along with other unknown and unidentified enzyme systems. This fact indicates that the glucose polymer mixtures of this invention will be utilized by human diabetic patients.

EXAMPLE 1

A human patient received a continuous injection via a peripheral vein of a substantially clear, nonpyrogenic, stable and sterile solution isotonic to human blood and comprising a glucose polymer mixture having an average degree of polymerization of 5 and at least 99% of its molecules less than 26 glucose units, at least 85% of its molecules less than 11 glucose units, and at least 20% of its molecules less than 4 glucose units. The described isotonic solution was infused at a rate of 2.5 mg. of glucose polymer/min./kg. of the patient's body weight for 3 hours. Urine samples were collected every 30 minutes. After 6 hours, only 7% of the infused glucose polymer mixture had appeared in the urine, indicating that 93% of the mixture had been retained for utilization by the patient's body.

EXAMPLE 2

A second human patient received an identical infusion as that administered in Example 1. After 6 hours, only 2% of the infused glucose polymer mixture had appeared in the urine, indicating that 98% of the mixture had been retained for utilization by the patient's body.

EXAMPLE 3

A third human patient received an infusion identical to that administered in Example 1, except that it was infused at a rate of 5.0 mg. of glucose polymer mixture/min./kg. of the patient's body weight. After 6 hours, 67% of the infused glucose polymer mixture had appeared in the urine.

EXAMPLE 4

A fourth human patient received an infusion identical to that administered in Example 3. After 6 hours, 59% of the infused glucose polymer mixture had appeared in the urine.

EXAMPLE 5

Five human patients received an infusion of maltose in a peripheral vein for 12 hours continuously at a rate of 2.5 mg. of maltose/min./kg. of patient body weight. Urine samples were taken from the patients every 30 minutes. After 18 hours, from 14 to 20% of the maltose had appeared in the patient's urine.

EXAMPLE 6

Four human patients received an infusion of maltose identical to that administered in Example 5, except that each patient also received a concomitant subcutaneous injection of 15–16 units of insulin. After 18 hours, from 1 to 7% of the infused maltose had appeared in the patient's urine, thereby indicating enhanced utilization of the maltose because of the insulin injection.

EXAMPLE 7

Six human patients received an infusion of maltose identical to that of Example 5, except that the rate of infusion was 5.0 mg. of maltose/min./kg. of patient body weight. After 18 hours, from 40 to 48% of the infused maltose had appeared in the patient's urine.

EXAMPLE 8

Four human patients received an infusion of maltose identical to that of Example 7, except that each patient also received a concomitant subcutaneous injection of 24–30 units of insulin. After 18 hours, from 21 to 39% of the maltose had appeared in the patient's urine, thereby indicating enhanced utilization of the maltose because of the insulin injection.

Preferred solutions of the present invention are further characterized as comprising 20–30% W/V of a glucose polymer mixture having an average degree of polymerization between 4 and 6, less than 1% of its molecules greater than 25 glucose units, 4 to 10% of its molecules between 11 and 25 glucose units, 1 to 3% of its molecules 10 glucose units, 3 to 5% of its molecules 9 glucose units, 5 to 8% of its molecules 8 glucose units, 14 to 17% of its molecules 7 glucose units, 16 to 18% of its molecules 6 glucose units, 8 to 9% of its molecules 5 glucose units, 10 to 13% of its molecules 4 glucose units, 13 to 17% of its molecules 3 glucose units, 8 to 13% of its molecules 2 glucose units, and 1 to 3% of its molecules 1 glucose unit. They have been prepared as illustrated in the following examples.

EXAMPLE 9

A starch hydrolysate having a dextrose equivalent of 10–13 and consisting of 1% glucose, 4% maltose, 5% maltotetraose, 4% maltopentaose and 82% molecules of six or more glucose units was subjected to reverse osmosis according to the teachings of U.S. Pat. No. 3,756,853 granted to G. Meyer on Sept. 4, 1973 and entitled "Process for the Production of Nonhazing Starch Conversion Syrups," which teachings are incorporated herein by this reference thereto. After fractionating the solution through a 1000 molecular weight cut-off and a 600 molecular weight cut-off membrane, the resulting glucose polymer mixture was found to comprise 2.6% glucose, 8.8% maltose, 12.6% maltotriose, 10.0% maltotetraose, 8.0% maltopentaose, 17.4% maltohexaose, 18.1% maltoseptaose, 8.9% maltooctaose, 5.1% maltononaose, 2.8% maltodecaose, and 5.7% 11–13 glucose units.

EXAMPLE 10

A starch hydrolysate having a dextrose equivalent of 10–13 and consisting of 1% glucose, 4% maltose, 5% maltotriose, 4% maltotetraose, 4% maltopentaose and 82% molecules of six or more glucose units was dissolved in distilled water. That solution was then added to Ethanol 3A, 200 proof with agitation. (The preferred alcohol concentration is 70–95%). After 30 minutes agitation, a diatomaceous earth filter aid was added. Agitation was continued for 30 more minutes and then stopped allowing the solids to separate. The supernatant liquid was decanted, filtered and transferred to a concentrator. This procedure was repeated 24 times. The filtered supernatant solutions were combined and concentrated to remove the ethanol. An aqueous solution of the concentrated supernatant was treated with activated carbon and then passed through two ion exchange resin columns. The effluent solution was spray dried to produce a dry product.

EXAMPLE 11

The procedure of Example 10 is followed beginning with a starch hydrolysate having a dextrose equivalent of 16–20 and consisting of 1% glucose, 7% maltose, 9% maltotriose, 6% maltotetraose, 6% maltopentaose and 71% molecules of six or more glucose units.

EXAMPLE 12

The procedure of Example 10 is followed beginning with a starch hydrolysate having a dextrose equivalent of 13–17 and consisting of 1% glucose, 3% maltose, 8% maltotriose, 6% maltotetraose and 82% molecules of five or more glucose units.

EXAMPLE 13

The procedure of Example 10 is followed beginning with a starch hydrolysate having a dextrose equivalent of 18–22 and consisting of 1% glucose, 6% maltose, 8% maltotriose, and 78% molecules of five or more glucose units.

EXAMPLE 14

U.S. Pat. No. 3,668,007 granted to C. Egger, et al. on June 6, 1972 and entitled "Syrup Fractionation Process" teaches the fractionation of starch hydrolysates by both ultrafiltration and reverse osmosis. The teachings thereof are incorporated herein by this reference thereto. If the teachings of U.S. Pat. No. 3,668,007 are employed in Example 9, substantially identical results will be obtained.

EXAMPLE 15

When a dry glucose polymer mixture product obtained from the procedure of Example 10 was added to distilled water in amounts producing a 25% W/V solution and subjected to steam sterilization or autoclaving, chemical testing of the resulting solution showed that it had an average degree of polymerization of substantially 5, was visually clear when viewed in a light box, had a color between 40 and 50 APHA units, had a pH of substantially 4.2 and a glucose polymer mixture distribution of 2.0% glucose, 8.4% maltose, 13.4% maltotriose, 10.5% maltotetraose, 8.7% maltopentaose, 17.3% maltohexaose, 16.4% maltoseptaose, 7.4% maltooctaose, 4.2% maltononaose, 2.8% maltodecaose, 8.8% 11–25 glucose units and 0.7% glucose units greater than 25. The solutions were determined to be stable even during steam sterilization.

EXAMPLE 16

When another dry glucose polymer mixture product obtained from the procedure of Example 10 was added to distilled water in amounts producing a 25% W/V solution and subjected to steam sterilization, chemical testing of the resulting solution showed that it had an average degree of polymerization of substantially 5, was visually clear when viewed in a light box, had a color between 40 and 50 APHA units, had a pH of substantially 4.2 and a glucose polymer mixture distribution of 3.0% glucose, 12.3% maltose, 16.8% maltotriose, 12.2% maltotetraose, 8.5% maltopentaose, 16.6% maltohexaose, 14.5% maltoseptaose, 5.9% maltooctaose, 3.2% maltononaose, 1.9% maltononaose, 4.5% 11-25 glucose units and 0.7% glucose units greater than 25. The solutions were determined to be stable even during steam sterilization.

That which we claim is:

1. A substantially clear, nonpyrogenic, stable and sterile solution for intravenous administration to human patients, said solution comprising at least 20% W/V of a glucose polymer mixture having an average degree of polymerization of at least 4 and at least 99% of its molecules less than 26 glucose units, at least 85% of its molecules less than 11 glucose units, and at least 20% of its molecules less than 4 glucose units.

2. The solution defined in claim 1, wherein said solution comprises from 20 to 50% W/V of said glucose polymer mixture.

3. The solution defined in claim 2, wherein said solution is isotonic to human blood.

4. The solution defined in claim 3 wherein said glucose polymer mixture has an average degree of polymerization between 4 and 10.

5. The solution defined in claim 1, wherein said glucose polymer mixture has an average degree of polymerization between 4 and 10.

6. The solution defined in claim 1, wherein said solution comprises from 20-30% W/V of a glucose polymer mixture having an average degree of polymerization between 4 and 6, less than 1% of its molecules greater than 25 glucose units, 4 to 10% of its molecules between 11 and 25 glucose units, 1 to 3% of its molecules 10 glucose units, 3 to 5% of its molecules 9 glucose units, 5 to 8% of its molecules 8 glucose units, 14 to 17% of its molecules 7 glucose units, 16 to 18% of its molecules 6 glucose units, 8 to 9% of its molecules 5 glucose units, 10 to 13% of its molecules 4 glucose units, 13 to 17% of its molecules 3 glucose units, 8 to 13% of its molecules 2 glucose units, and 1 to 3% of its molecules 1 glucose unit.

7. A method of providing calories to a human patient comprising infusing into a peripheral vein of said patient a clear, nonpyrogenic, stable and sterile solution including at least 20% W/V of a glucose polymer mixture having an average degree of polymerization of at least 4 and at least 99% of its molecules less than 26 glucose units, at least 85% of its molecules less than 11 glucose units, and at least 20% of its molecules less than 4 glucose units.

8. The method of providing calories defined in claim 7 wherein said solution comprises from 20 to 50% W/V of said glucose polymer mixture.

9. The method of providing calories defined in claim 8, wherein said solution is isotonic to human blood.

10. The method of providing calories defined in claim 9, wherein said glucose polymer mixture has an average degree of polymerization between 4 and 10.

11. The method of providing calories defined in claim 7, wherein said glucose polymer mixture has an average degree of polymerization between 4 and 10.

12. The method of providing calories defined in claim 7, wherein said solution comprises from 20-30% W/V of a glucose polymer mixture having an average degree of polymerization between 4 and 6, less than 1% of its molecules greater than 25 glucose units, 4 to 10% of its molecules between 11 and 25 glucose units, 1 to 3% of its molecules 10 glucose units, 3 to 5% of its molecules 9 glucose units, 5 to 8% of its molecules 8 glucose units, 14 to 17% of its molecules 7 glucose units, 16 to 18% of its molecules 6 glucose units, 8 to 9% of its molecules 5 glucose units, 10 to 13% of its molecules 4 glucose units, 13 to 17% of its molecules 3 glucose units, 8 to 13% of its molecules 2 glucose units, and 1 to 3% of its molecules 1 glucose unit.

13. A method of providing calories to a diabetic human patient without increasing said patient's blood glucose level comprising infusing into a peripheral vein of said diabetic patient a clear, nonpyrogenic, stable and sterile solution including at least 20% W/V of a glucose polymer mixture having an average degree of polymerization of at least 4 and at least 99% of its molecules less than 26 glucose units, at least 85% of its molecules less than 11 glucose units, and at least 20% of its molecules less than 4 glucose units.

14. The method of providing calories to a diabetic patient as defined in claim 13, wherein said solution comprises from 20 to 50% W/V of said glucose polymer mixture.

15. The method of providing calories to a diabetic patient as defined in claim 14, wherein said solution is isotonic to human blood.

16. The method of providing calories to a diabetic patient as defined in claim 15, wherein said glucose polymer mixture has an average degree of polymerization between 4 and 10.

17. The method of providing calories to a diabetic patient as defined in claim 13, wherein said glucose polymer mixture has an average degree of polymerization between 4 and 10.

18. The method of providing calories to a diabetic patient as defined in claim 13, wherein said solution comprises from 20-30% W/V of a glucose polymer mixture having an average degree of polymerization between 4 and 6, less than 1% of its molecules greater than 25 glucose units, 4 to 10% of its molecules between 11 and 25 glucose units, 1 to 3% of its molecules 10 glucose units, 3 to 5% of its molecules 9 glucose units, 5 to 8% of its molecules 8 glucose units, 14 to 17% of its molecules 7 glucose units, 16 to 18% of its molecules 6 glucose units, 8 to 9% of its molecules 5 glucose units, 10 to 13% of its molecules 4 glucose units, 13 to 17% of its molecules 3 glucose units, 8 to 13% of its molecules 2 glucose units, and 1 to 3% of its molecules 1 glucose unit.

19. In the method of providing calories to human patients by intravenously feeding the patient an aqueous carbohydrate solution, the improvement which comprises, infusing into a peripheral vein of said patient a clear, nonpyrogenic, stable and sterile solution comprising glucose polymers having molecules substantially all less than 26 glucose units in length at a rate providing said patient not more than 5 milligrams of glucose polymers a minute for each kilogram of said patient's body weight.

20. The method of providing calories defined in claim 19, wherein said rate of infusion provides between 2 and 3 milligrams of glucose polymer a minute for each kilogram of said patient's body weight.

21. The method of providing calories defined in claim 19, wherein said aqueous solution of glucose polymers is a 10-50% W/V solution.

22. The method of providing calories defined in claim 21, wherein said aqueous solution of glucose polymers is substantially isotonic with human blood.

23. The method of providng calories defined in claim 19, wherein said glucose polymers in said aqueous solution consist essentially of maltose.

24. The method of providing calories defined in claim 19, wherein said glucose polymers have an average degree of polymerization of at least 4 and are further defined in that at least 85% of the polymers are less than 11 glucose units.

25. The method of providing calories defined in claim 24, wherein said glucose polymers have an average degree of polymerization between 4 and 10.

26. The method of providing calories defined in claim 19, wherein said solution comprises from 20-30% W/V of a glucose polymer mixture having an average degree of polymerization between 4 and 6, less than 1% of its molecules greater than 25 glucose units, 4 to 10% of its molecules between 11 and 25 glucose units, 1 to 3% of its molecules 10 glucose units, 3 to 5% of its molecules 9 glucose units, 5 to 8% of its molecules 8 glucose units, 14 to 17% of its molecules 7 glucose units, 16 to 18% of its molecules 6 glucose units, 8 to 9% of its molecules 5 glucose units, 10 to 13% of its molecules 4 glucose units, 13 to 17% of its molecules 3 glucose units, 8 to 13% of its molecules 2 glucose units, and 1 to 3% of its molecules 1 glucose unit.

27. A method of preparing a clear, nonpyrogenic, stable and sterile solution for intravenous administration to human patients comprising:
(a) dissolving a corn starch hydrolysate having a dextrose equivalent of 10-25 in distilled water to form a corn starch hydrolysate solution,
(b) adding alcohol to said solution to obtain an alcohol concentration of 70 to 95%,
(c) agitating said solution,
(d) terminating said agitation of said solution and allowing said solution to remain calm until it separates into supernatant and precipitants portions,
(e) decanting said supernatant portion from said solution into a collection container,
(f) repeating steps c, d and e a plurality of times,
(g) removing said alcohol from said plurality of supernatant portions in said collection container by concentrating said plurality of supernatant solutions,
(h) dissolving said concentrated supernatant in distilled water to form a concentrated supernatant solution, then, treating with activated carbon and filtering said concentrated supernatant solution,
(i) drying said filtered concentrated supernatant solution to produce a dried glucose polymer mixture,
(j) dissolving an amount of said dried glucose polymer mixture into an amount of distilled water in a predetermined ratio to form a preferred % W/V solution, and
(k) autoclaving said preferred % W/V solution.

28. The method of claim 27, wherein said corn starch hydrolysate has a dextrose equivalent of 10-13 and consists of 1% glucose, 4% maltose, 5% maltotriose, 4% maltotetraose, 4% maltopentaose and 82% molecules of six or more glucose units.

29. The method of claim 27, wherein said corn starch hydrolyzate has a dextrose equivalent of 16-20 and consists of 1% glucose, 7% maltose, 9% maltotriose, 6% maltotetraose, 6% maltopentaose and 71% molecules of six or more glucose units.

30. The method of claim 27, wherein said corn starch hydrolysate has a dextrose equivalent of 13-17 and consists of 1% glucose, 3% maltose, 8% maltotriose, 6% matotetraose and 82% molecules of five or more glucose units.

31. The method of claim 27, wherein said corn starch hydrolysate has a dextrose equivalent of 18-22 and consists of 1% glucose, 6% maltose, 8% maltotriose, 7% maltotetraose, and 78% molecules of five or more glucose units.

32. The method of claim 27, wherein said distilled water is between 30°-45° C. when said corn starch hydrolysate is dissolved therein and said corn starch hydrolysate solution is maintained between 20°-35° C. during said agitation of said corn starch hydrolysate solution.

33. The method of claim 27, wherein said alcohol is ethanol 3A, 190-200 proof.

34. The method of claim 27, wherein said filtered concentrated supernatant solution is dried by spray drying.

35. The method of claim 27, wherein diatomaceous earth is added to said corn starch hydrolysate solution during said agitation of said corn starch hydrolysate solution.

36. The method of claim 27, wherein said supernatant portion of said corn starch hydrolysate solution is filtered before said supernatant portion enters said collection container.

37. The method of claim 27, wherein said filtered concentrated supernatant solution is passed through an ion exchange resin before it is spray dried.

38. A method of preparing a clear, nonpyrogenic, sterile and stable solution for intravenous administration to human patients comprising:
(a) dissolving a corn starch hydrolysate having a dextrose equivalent of 10-25 in distilled water to form a corn starch hydrolysate solution,
(b) subjecting said corn starch hydrolysate to fractionation through a semipermeable membrane to obtain a preferred glucose polymer mixture,
(c) dissolving an amount of said glucose polymer mixture into an amount of distilled water in a predetermined ratio to form a preferred % W/V solution, and
(d) autoclaving said preferred % W/V solution.

39. The method of claim 38, wherein said corn starch hydrolysate has a dextrose equivalent of 10-13 and consists of 1% glucose, 4% maltose, 5% maltotriose, 4% maltotetraose, 4% maltopentaose and 82% molecules of six more more glucose units.

40. The method of claim 38, wherein said corn starch hydrolysate has a dextrose equivalent of 16-20 and consists of 1% glucose, 7% maltose, 9% maltotriose, 6% maltotetraose, 6% maltopentaose and 71% molecules of six or more glucose units.

41. The method of claim 38, wherein said corn starch hydrolysate has a dextrose equivalent of 13-17 and consists of 1% glucose, 3% maltose, 8% maltotriose, 6% maltotetraose and 82% molecules of five or more glucose units.

42. The method of claim 38, wherein said corn starch hydrolysate has a dextrose equivalent of 18-22 and consists of 1% glucose, 6% maltose, 8% maltotriose, 7% maltotetraose, and 78% molecules of five or more glucose units.

43. The method of claim 38 wherein said corn starch hydrolysate is subjected to reverse osmosis through said semipermeable membrane.

44. The method of claim 38 wherein said corn starch hydrolysate is subjected to ultrafiltration through said semipermeable membrane.

45. The method of claim 38 wherein said preferred glucose polymer mixture is further refined by treatment with activated carbon before it is dissolved in said distilled water to form said preferred % W/V solution.

46. The method of claim 38 wherein said preferred glucose polymer mixture is spray dried before it is dissolved in said distilled water to form said preferred % W/V solution.

* * * * *